United States Patent
Amiral et al.

(10) Patent No.: US 9,097,731 B2
(45) Date of Patent: Aug. 4, 2015

(54) METHOD AND KIT FOR THE DETECTION OF HEPARIN-DEPENDENT ANTIBODIES AND THE DIAGNOSIS OF IMMUNE OR AUTOIMMUNE PATHOLOGIES POTENTIATED BY HEPARIN, SUCH AS HEPARIN-INDUCED THROMBOCYTOPENIA

(75) Inventors: Jean Amiral, Neuville sur Oise (FR); Anne-Marie Vissac, Neuville sur Oise (FR)

(73) Assignee: Hypen Biomed, Neuvill Sur Oise (FR)

( * ) Notice: Subject to any disclaimer, the term of this patent is extended or adjusted under 35 U.S.C. 154(b) by 1299 days.

(21) Appl. No.: 12/305,224

(22) PCT Filed: Jun. 25, 2007

(86) PCT No.: PCT/FR2007/001049
§ 371 (c)(1),
(2), (4) Date: Jun. 3, 2009

(87) PCT Pub. No.: WO2007/147983
PCT Pub. Date: Dec. 27, 2007

(65) Prior Publication Data
US 2010/0015647 A1    Jan. 21, 2010

(30) Foreign Application Priority Data
Jun. 23, 2006 (FR) .................... 06 05662

(51) Int. Cl.
*G01N 33/543* (2006.01)
*G01N 33/86* (2006.01)
(52) U.S. Cl.
CPC ............ *G01N 33/86* (2013.01); *G01N 2400/40* (2013.01); *G01N 2800/222* (2013.01)
(58) Field of Classification Search
None
See application file for complete search history.

(56) References Cited

U.S. PATENT DOCUMENTS

| | | | | |
|---|---|---|---|---|
| 5,466,582 A | * | 11/1995 | Amiral | 435/7.9 |
| 5,753,445 A | | 5/1998 | Fillet et al. | |
| 5,972,717 A | | 10/1999 | Aster et al. | |
| 7,011,953 B2 | * | 3/2006 | Abdelouahed et al. | 435/7.21 |
| 2006/0172438 A1 | * | 8/2006 | Milunic et al. | 436/524 |

OTHER PUBLICATIONS

Levine et al., Human Platelet Factor 4: Purification and characterization by Affinity Chromatography, The Journal of Biological Chemistry, vol. 251, No. 2, Jan. 1976, pp. 324-328.*

John L. Francis, Ph.D. "A Critical Evaluation of Assays for Detecting Antibodies to the Heparin-PF4 Complex", Seminars in Thrombosis and Hemostasis, Stuttgart, DE, vol. 30, No. 3, 2004, pp. 359-368.

* cited by examiner

*Primary Examiner* — Gary W Counts
(74) *Attorney, Agent, or Firm* — Trego, Hines & Ladenheim, PLLC

(57) ABSTRACT

A method for the detection of heparin-dependent antibodies and the diagnosis of immune or autoimmune pathologies potentiated by a heparin substance, such as thrombocytopenia induced by heparin (HIT type II) as inducer drug. The method includes the steps of reacting at least one substance with high affinity for a heparin substance (SFA), with at least one heparin substance (SH) so as to form a substance with high affinity for heparin-heparin substance (SFA-SH) complex. The heparin substance is adapted to bind other substances with affinity for heparin and with at least one potential antigenic substance capable of reacting with the heparin substance, forming a (Ag-SH) complex. The method further includes the steps of testing a patient's plasma or serum potentially containing an anti(Ag-SH) antibody after administration of the heparin substance and revealing the resulting (Ag-SH)-anti(Ag-SH) complex produced.

19 Claims, 2 Drawing Sheets

METHOD AND KIT FOR THE DETECTION
OF HEPARIN-DEPENDENT ANTIBODIES
AND THE DIAGNOSIS OF IMMUNE OR
AUTOIMMUNE PATHOLOGIES
POTENTIATED BY HEPARIN, SUCH AS
HEPARIN-INDUCED THROMBOCYTOPENIA

BACKGROUND OF THE INVENTION

The present invention relates to a rapid, effective, economical and sensitive method for the detection of antibodies induced by a heparin substance and the diagnosis of immune or autoimmune pathologies potentiated by a heparin substance, such as heparin-induced thrombocytopenia (HIT type II). The invention also relates to a kit for the detection of heparin-dependent antibodies and the diagnosis of pathologies potentiated by a heparin substance, such as heparin-induced thrombocytopenia.

Thrombopenias or thrombocytopenias may be of many origins. They may be produced by the presence of drugs, notably quinine/quinidine, pentosan polysulfate, but above all heparin. (See article by M. C. Berndt et al., *Blood Reviews* 1, pages 111-118 (1987) and article by B. Tardy-Poncet, *Am J Hematol* 2994; 45(3): 252-7).

Heparin is administered to patients as an anti-coagulant factor for preventing risks of venous or arterial thromboses. However, certain patients treated with heparin develop antibodies induced by heparin, resulting in thrombocytopenia, which may be very severe or even fatal. These thrombocytopenias appear to be produced by IgG, IgM or IgA antibodies, which develop after 5 or more days of treatment with heparin. Antibodies of isotype IgG are by far the most pathogenic.

This reaction takes place at a "critical concentration" of heparin (Y. Gruel, *Presse Med* 1998; 27 (Suppl. 2): 7-12 and T E Warkentin et al., *Chest* 2004; 126: 311S-37S).

Rapid identification of patients at risk of or developing this HIT type II pathology appears to be essential.

At the present time, the methods for diagnosis of thrombocytopenia are:
  blood platelet count before, during and after treatment, a long and not very specific method;
  search for the absence of an etiology other than a thrombocytopenia (infection, other therapies, etc.), a long and tedious method;
  use of biological tests seeking the presence of antibodies directed against platelets in the presence of the inducer drug;
  search for and measurement by ELISA method or some other immunologic method for antibodies directed against heparin and platelet factor 4 (pF4) complexes.

Of these biological tests, those principally used are platelet aggregation tests, which require suitable apparatus and the operational details of which are long and lack sensitivity.

Other methods that have been described [articles by J. G. Kelton et al., *Blood* 72 (No. 2), pages 925-930 (1988) and B. H. Chong, *British Journal of Haematology* 49, pages 531-540 (1988) and B. H. Chong, *Blood Reviews* 2, pages 108-114 (1986) and D. Sheridan et al., *Blood* 67 (No. 1), pages 27-30 (1986) and Y. Gruel, *Sang Thrombose Vaisseaux,* 1 (No. 4), pages 233-236 (1989)] employ study of platelet fixation of serum IgG, release of $^{14}$C-radiolabeled serotonin at two different concentrations of heparin, availability of platelet factor 4, fixation of the complement, inhibition of lysis of the complement and agglutination of sensitized red blood cells. These methods have the disadvantages of not being very sensitive or taking a long time to carry out.

Other methods that are sensitive and rapid in their performance, based on cytochemistry, use either marking of platelets activated or not, detected by flux cytometry, or purified factors issuing from platelets capable of preferentially binding to heparin and forming a complex with heparin-induced antibodies, or binding competition tests. All of these tests are performed with fresh platelets. Lastly, other immuno-cytochemical tests are done with heparin, plasma to be tested potentially containing heparin-induced antibodies and an antibody coupled to a reference molecule, but these last tests are performed without addition of platelets nevertheless necessary for sensitization of the test.

The determination of heparin-induced antibodies is essential in the prevention or treatment of HIT type II.

Several types of heparins are used:
  non-fractionated heparins (NFH), which induce the appearance of heparin-induced antibodies sooner and more frequently;
  heparins of low molecular weight.

However, it is possible to use any type of heparin derivatives or of negatively charged non-glycosaminoglycan linear polymers that are not carbohydrates, such as polyvinyl sulfate, polyvinyl sulfonate, polystyrene sulfonate, polyanethol sulfonate, polyvinyl phosphates and polyvinyl phosphonate, poly-D glutamate (see PCT/US97/02840 WO9732211).

It has been discovered that the use of factors having a high affinity for heparin are very promising because they permit biological tests to be more specific and sensitive. In effect, heparin-induced antibodies have long been considered to be directed against heparin itself, but since the antigenic target of the antibodies has been identified, notably as described in EP 0,495,971, as being stoichiometic complexes of heparin and of platelet factor, pF4, more and more information concerning the mechanisms involved is available. In effect, pF4, in binding to heparin so as to neutralize its anticoagulant properties, changes conformation and then becomes immunogenic.

In this method, the factors issuing from platelets having a high affinity for heparin or the antibody inducer drug and obtained by platelet cleavage or lysis are:
  platelet factor 4 or pF4
  fractions of this factor pF4
  fractions containing at least one substance washed out at the same time as pF4
  recombinant pF4 and its variants
  synthetic peptides absorbing all or part of the amino acid sequence of pF4
  proteoglycan
  proteoglycan-pF4 complexes
  and mixtures thereof.

However, such a method necessarily requires purification of platelet factor 4 (pF4) or the use of purified and functional recombinant pF4, which makes the method more complex and very burdensome.

U.S. Pat. No. 5,972,717 describes such a method for the detection of heparin-induced antibodies using a factor with high affinity for heparin adsorbed on a support, purified platelet factor pF4 and the serum or plasma of a patient to be tested. In this method, the factor with high affinity for heparin used is streptavidin, and it is used for the purpose of fixing the heparin molecule securely but especially for orienting it on the support. Further, use of the method as described requires the purification of pF4, a major disadvantage in terms of complexity and reliability as well as cost.

Another method for the detection of heparin-induced antibodies is described in the document entitled [in English:] "Antibodies to macromolecular platelet factor 4-heparin complexes in heparin-induced thrombocytopenia: a study of 44 cases," [end English] published in Thrombosis and Haemostasis, Vol. 73, No. 1, 1995, pages 21 to 28. For detecting antibodies binding to the pF4-heparin complex, this document describes an ELISA assay using a substance (MBSS) coating the wells of the plate, a pF4-heparin mixture, a goat serum and the plasma to be tested. Although such a method may be promising, it nevertheless has some limits, principally as concerns its cost and its detection. In effect, this ELISA assay requires an essential purification of the pF4 antigen, a disadvantage already pointed out above. Moreover, the method as described only permits detection of pF4-dependent antibodies, whereas in the diagnosis of immune or autoimmune heparin-induced pathologies, it would be particularly interesting and advantageous to be able to detect all heparin-induced antibodies, i.e., all antibodies induced by antigen-heparin complexes, the antigen not being limited to only pF4.

The majority of recent methods of the prior art relating to this detection of heparin-induced antibodies use fixing of said heparin on a support and addition of an antigenic substance, such as, for example, platelet factor pF4, glycosaminoglycan or proteoglycan polymers, permitting formation of the complex generating detectable heparin-dependent antibodies. Nevertheless, all the documents of the prior art (U.S. Pat. No. 5,972,717, U.S. Pat. No. 5,753,445, U.S. Pat. No. 5,972,718, U.S. Pat. No. 5,466,582, the article entitled "Antibodies to macromolecular platelet factor 4-heparin complexes in heparin-induced thrombocytopenia: a study of 44 cases," published in Thrombosis and Haemostasis, Vol. 73, No. 1, 1995, pages 21 to 28, the article entitled [in English:] "Polyarginine as a multifunctional fusion tag," published in Protein Science: A publication of the Protein Society, June 2005, Vol. 14, No. 6, June 2005 (2005-06), pages 1538-1544) require at least one step of purification of the material used, which considerably increases the cost of the method. Thus, in the light of the prior art set forth above, it was necessary to perfect a method for the detection of heparin-induced antibodies at reduced cost and with increased sensitivity.

BRIEF SUMMARY OF THE INVENTION

The object of the present invention therefore is to propose a method for detection and diagnosis, making it possible to obtain, in this kind of test in immunocytochemistry, better sensitivity and very good results in the detection of antibodies and the diagnosis of immune or autoimmune pathologies potentiated by a heparin substance including HIT type II, while being economically more advantageous.

According to the invention, for the detection of antibodies induced by a heparin substance, also called heparin-dependent antibodies, and for the diagnosis of immune or autoimmune pathologies by a heparin substance, including HIT type II, as inducer drug, use will be made of the method characterized in that it comprises the steps consisting in:
1) reacting:
at least one substance with high affinity for a heparin substance (SFA), consisting of any molecule or complex having a high affinity for a heparin substance, with at least one heparin substance (SH) so as to form a substance with high affinity for heparin-heparin substance (SFA-SH) complex, wherein the heparin substance is in slight or large excess, so as to be able to bind other substances with affinity for heparin;
with at least one potential antigenic substance capable of reacting with the heparin substance, thus forming a complex (Ag-SH);
and with the plasma or the serum of a patient to be tested (preferably diluted to a dilution of the order of 1:100) potentially containing: an anti(Ag-SH) antibody material generated in the organism after administration of a heparin substance and which recognizes (Ag-SH), according to the reaction:

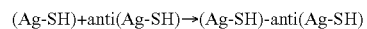

and/or one immune complex consisting of an Ag-SH-anti(Ag-SH) antibody complex present in the plasma or serum of the patient capable of reacting with the substance with high affinity for the heparin substance-heparin substance (SFA-SH) complex,
then
2) revealing the resulting (Ag-SH)-anti(Ag-SH) complex produced.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1:
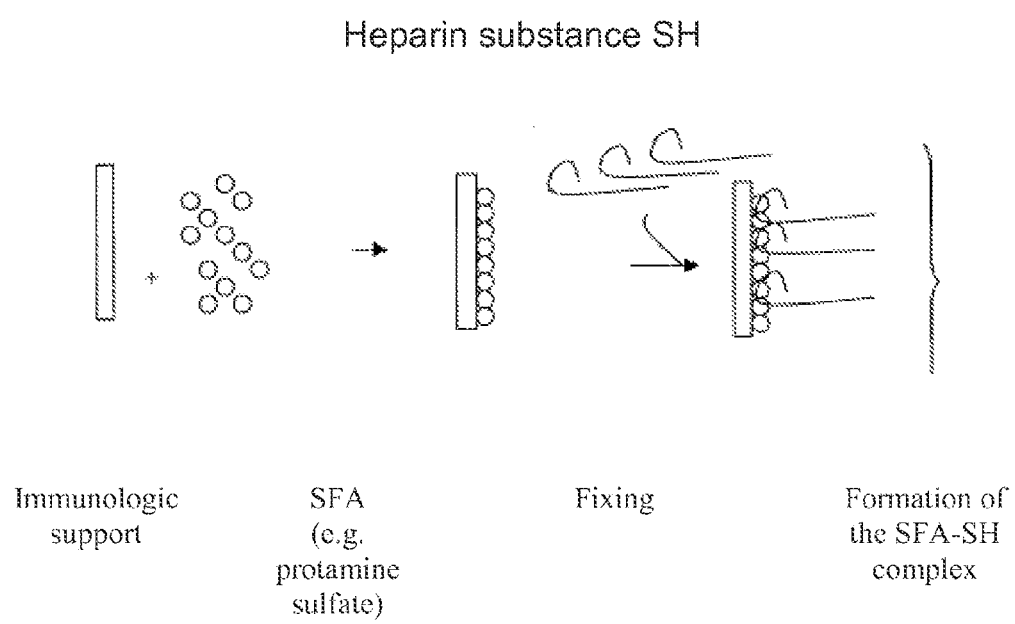
FIG. 1 illustrates a reaction that forms an SFA-SH complex.

For the sake of easier readability, the term anti(Ag-SH) will include the anti(Ag-SH) antibody as well as the immune complex form Ag-SH-anti(Ag-SH) complex potentially present in the serum or the plasma to be tested. This immune complex is capable of reacting with the SFA-SH complex described above. This method of detection according to the invention thus also permits determination of the immune complexes circulating in the serum or the plasma of the patient.

At least one substance with high affinity for a heparin substance (SFA), such as, preferably, protamine sulfate, streptavidin (in this case, the heparin substance is necessarily biotinylated, streptavidin having an affinity for heparin owing to the bias of biotin), poly-L-lysine, polyarginine, polybrene, immobilizes at least one heparin substance in excess (SH), which, in turn, will fix the molecules with affinity for the heparin substance (including pF4), thus forming the complex (Ag-SH). This (Ag-SH) complex will be recognized by the specific anti(Ag-SH) antibodies directed against it and contained in the plasma or the serum of the patient to be tested forming the (Ag-SH)-anti(Ag-SH) complex.

This same complex will be detected by a variety of techniques known to those skilled in the art, detailed below. In comparison with preceding approaches, this approach with the substance with high affinity for a heparin substance such as protamine sulfate, streptavidin, poly-L-lysine, polyarginine, polybrene, has the principal advantages of speed, of specificity and of detection of all heparin-dependent (and not only pF4-dependent) antibodies, at a very competitive cost of performance, with great sensitivity and with the possibility to be carried out by ultra-rapid individual techniques.

This method of detection may be carried out in many known technologies: ELISA assay, immunoturbidimetry, agglutination of latex on slides, nephelometry, turbidimetry or nephelometry enhanced by latex particles, immunofluorescence (slide, microplate, fluorescent latex, magnetic latex, test on membranes, biochips, etc.), and in general, any method permitting identification and/or quantification of a reaction between an antigen (including haptenes) and an antibody, of an isotype of any kind.

The potential antigenic substance(s) capable of reacting with the heparin substance to form the (Ag-SH) complex may come directly from the plasma or the serum of the patient to be tested. In this case, however, the concentration of these substances may then be a factor limiting the sensitivity of the test.

Consequently, according to a first preferred variant of the method according to the invention, the at least one potential antigenic substance may be supplied in excess by a platelet lysate made up of a concentrate of normal platelets (mixture of several donors, for example), lysed (by destruction of the platelets), or a leukocyte lysate (concentrate of normal leukocytes). This variant permits maximum sensitization of the method, the potential antigenic substance or substances being supplied in sufficient quantity, and preferably in excess, to be able to react with the heparin substance to form the (Ag-SH) complex.

According to another also very advantageous variant of the method, the at least one potential antigenic substance capable of reacting with the heparin substance may be supplied by any biological medium containing it. Thus, if necessary, if the platelet concentrate or the leukocyte concentrate or the patient's tested sample does not contain the substance with affinity for the heparin substance in sufficient quantity, and potential antigen, the latter could be provided by any biological medium containing it. Accordingly, this technique is extensible to any antigen formed by complexation with the heparin substance, or any substance having similar properties, such as defined above, and capable of reacting with the antibodies present in immune or autoimmune pathological conditions potentiated by a heparin substance, such as heparin-induced thrombocytopenia.

The method of detection of the present invention proceeds according to the following steps:

1) Fixing by adsorption or by covalent binding of at least one substance having high affinity for a heparin substance (SFA) on an essentially solid support, or any other reactive support permitting an immunologic test to be performed. This SFA is usually protamine sulfate because it has the advantage of being very inexpensive and readily available; in a variant, fixing may relate to streptavidin (the heparin substance then being biotinylated) but also poly-L-lysine or polyarginine, according to the same methods as for protamine sulfate.

2) Addition of at least one heparin substance (if necessary, biotinylated) in excess.

3) Formation of a substance with high affinity for the heparin substance-heparin substance complex (or FSA-SH). At least one wash for removing the excess of heparin.

4) Optionally, sensitization if necessary by addition of a global platelet lysate coming from a platelet concentrate prepared from platelets of normal donors or a leukocyte lysate, and containing potentially antigenic molecules with affinity for the heparin substance and called antigenic substances.

5) Formation of an antigenic substance-heparin substance complex (or Ag-SH).

6) Addition of the plasma or the serum of the patient to be tested containing:
   a. substances complexing to the heparin substance to become potentially antigenic and
   b. potentially heparin-induced (Ag-SH) antibodies, optionally also in the form of immune complexes.

7) Following the serum or the plasma tested, formation of (Ag-SH)-anti(Ag-SH) complexes. At least one wash to eliminate any substance that might interfere with the detection system.

8) Addition of antibodies directed against anti-(Ag-SH) antibodies. These antibodies are detectable by marking according to known techniques described below (enzymoimmunology, radioimmunology, etc.).

9) Formation of (Ag-SH)-anti(Ag-SH)-anti(anti-Ag-SH) complexes. Washes.

10) Revelation of marking by immunological techniques or any other method permitting identification of the formation of complexes. Detection and determination of the antibodies induced by the heparin substance and responsible for heparin-induced thrombocytopenias (HIT type II).

11) Diagnosis.

In a variant in steps 8 to 10, one may use techniques permitting direct detection of antibodies as complexes with the antigen, such as refractometry, diffraction of light rays by the reactive surface, methods of modification of electrical conductivity or of the magnetic field, etc.

The originality of the present invention is that it permits perfection of a method capable of binding and measuring all the heparin-dependent antibodies responsible for HIT type II, regardless of whether they are free (anti(Ag-SH)) or complexed to the antigen (SH-Ag-anti(Ag-SH)), this thanks to the use of a substance with high affinity for a heparin substance, preferably protamine sulfate or streptavidin (associated with biotinylated heparin), which immobilizes the heparin on the reactive surface. Because of its wide availability, its ease of obtainment and low cost, this novel method (and its variants) makes it possible to increase the speed, sensitivity and reproducibility of the test and thus the diagnosis of patients at risk of or developing thrombocytopenia induced by heparin.

A substance with high affinity for a heparin substance (SFA) is adsorbed on or bound by covalence to a reactive support described below. This substance with high affinity for a heparin substance serves as an "anchor" for fixing the heparin or the heparin substance and thus increasing the reactive surface of the support. In particular, a complex at a concentration of from 0.01 to 1000 µg/cm$^2$ of reactive surface is obtained. The reaction that takes place as a result of the reactive support described above is best illustrated in FIG. 1.

The substance with high affinity for the heparin substance, such as protamine sulfate, streptavidin (associated with a biotinylated heparin substance), poly-L-lysine, polyarginine, polybrene, serves to fix the heparin substance according to reaction (A), and then this heparin substance will fix the antigenic substance possibly issuing from a global platelet lysate if this step has been performed, or from the serum or plasma of the patient to be tested. This antigenic substance-heparin substance complex (Ag-SH) can then be recognized by the antibodies induced by the heparin substance according to reaction (B) (see below) if such antibodies are present in the plasma or the serum of the patient to be tested. This will make it possible to finish detecting subjects at risk of or developing HIT type II, thanks to the present invention.

In a preferred embodiment of the invention, protamine sulfate is used as substance having a high affinity for the heparin substance.

In another preferred embodiment, streptavidin is used as substance with high affinity for the heparin substance (SFA), the heparin substance being in biotinylated form.

In still another preferred embodiment of the invention, poly-L-lysine, polyarginine or polybrene is used as substance having a high affinity for the heparin substance.

This protamine sulfate may have a variety of origins, generally being extracted from the sperm of salmon. To be more precise, the substance with high affinity for the heparin substance is in fact used here as anchoring support. Streptavidin is extracted from the egg of birds, but any substance having the same properties as protamine sulfate or streptavidin, and in particular any recombinant or synthesized molecule, may be used instead.

Advantageously, in the present invention, the heparin substance used may be of several natures and it may be represented by:
  non-fractionated heparin (HNF), which induces the appearance of heparin-induced antibodies sooner and more frequently. This heparin has an average molecular weight of 6000-30000 daltons and a rotational force $[\alpha]_D^{20}$ of about +55°;
  heparin of low molecular weight;
  compounds which derive from heparin such as metallic heparinates ($Ca^{2+}$, $Li^+$, $Na^+$, $Mg^{2+}$, etc.) and fragments of heparin;
  analogs of heparin such as heparinoids (heparamine and its salts, chondroitins and their salts, etc.);
  substances containing heparin, its derivatives and analogs such as complexes of heparin and of its derivatives or analogs;
  mixtures thereof;
  any of the molecules above in biotinylated form.

However, it is also possible to use as the heparin substance in the present invention pentosan polysulfate, any negatively charged sulfated polysaccharide or sulfated polymers of polystyrene such as negatively charged non-glycosaminoglycan linear polymers which are not carbohydrates, for example polyvinyl sulfate, polyvinyl sulfonate, polystyrene sulfonate, polyanethol sulfonate, polyvinyl phosphate and polyvinyl phosphonate, poly-D glutamate, or their biotinylated forms in the case of streptavidin, as the substance with high affinity for the heparin substance.

It is to be noted that the origin, the length of the polysaccharide chains and the degree of sulfatation of heparin substances appear to play an important role in their immunogenicity and hence in the development of HIT type II. In effect, heparin of bovine origin would appear to be more immunogenic than porcine heparin. On the other hand, non-fractionated heparins would also appear to be more immunogenic (5 to 20 times greater) than heparins of low molecular weights, but because of the more frequent and prolonged use of the latter, cases of HIT type II induced by these heparins have been described. Non-fractionated heparins are capable of "deforming" molecules with high affinity for heparin to a greater degree and generate complexes of greater size, inducing a stronger immune response.

The relative quantities of substance with high affinity for the heparin substance (SFA) and of heparin substance (SH) are: 1 mg of SFA for 100 to 100000 IU of heparin. Preferably, 1 mg of protamine sulfate [is used] for 100 to 1000 IU of heparin (but these proportions may vary in case of use of variants of protamine sulfate or of heparin). For streptavidin, 0.1 to 1000 μg of streptavidin is used for 0.1 to 100 IU of biotinylated heparin, and preferably 1 to 50 μg streptavidin for 0.5 to 20 IU of heparin, but since an excess is present, there is no constraint as to limit.

The potential antigenic substance or Ag is made up of a substance having a high affinity for heparin or a heparin substance described above. It comes from the plasma or the serum of the patient to be tested or optionally, if this is necessary, from a global platelet lysate. This antigenic substance will readily react with said heparin substance (previously fixed to the substance with high affinity for heparin, SFA, usually protamine sulfate or streptavidin, the heparin substance being biotinylated) and will thus form a complex with it, determined by the abbreviation (Ag-SH).

To avoid any confusion later, it is advisable to clarify this appellation:

The antigenic substance (for example, a factor derived from platelets) is called thus not because it by itself induces the production of antibodies, an immune response, but because once bound to the heparin substance for which it has a high affinity, it becomes immunogenic. Thus, the antigenic substance-heparin substance (Ag-SH) complex formed can then be recognized by the antibodies induced by heparin and potentially contained in the plasma and the serum of the patient to be tested. After suitable revelation, it will thus be possible to detect subjects at risk of or developing HIT type II, thanks to the present invention and according to the following reactions:

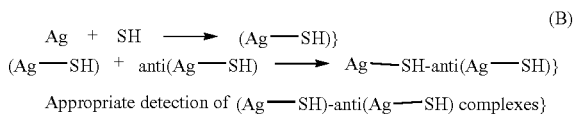

(B)

For the determination and diagnosis of immune or autoimmune pathologies potentiated by a heparin substance, such as heparin-induced thrombocytopenia (HIT type II) according to the invention, said antigenic substance will be selected from among the group of molecules or complexes having a high affinity for a heparin substance. These antigenic substances issue from the plasma or the serum of the patient or from a global platelet lysate or from a global leukocyte lysate or from any biological medium containing them. They may be:
  platelet factor 4 or pF4
  fractions of this factor pF4
  fractions containing at least one substance washed out at the same time as pF4
  recombinant pF4 and its variants
  synthetic peptides taking up all or part of the amino acid sequence of pF4
  proteoglycan
  proteoglycan-pF4 complexes
  as well as mixtures thereof
  beta-thromboglobulin
  NAP2
  PDGFs
  platelet glycoproteins
  interleukin-8 (IL-8)
  FGF (fibroblast growth factors), with high affinity for heparin,
  etc.

Previously, the antigenic substance was principally pF4, obtained from a purified platelet lysate, or functional and purified recombinant pF4, and served as antigenic target because, once complexed to the heparin substance, it induced the reaction of heparin-dependent antibodies. In the present invention, the heparin substance will be fixed to the reactive support defined below by a substance having a very high affinity for it (SFA, for example protamine sulfate, streptavidin, poly-L-lysine, polyarginine, polybrene), thus increasing the reactive surface of the reaction support. The antigenic substance recognized by the antibody could be pF4 because a global platelet lysate, containing among other things pF4, will be added to the SFA-heparin substance complex (for example, protamine sulfate-heparin). But all anti(Ag-SH) heparin-dependent antibodies will be able to be detected and not only those that depend on pF4. One of the major advantages of the present invention lies in the fact that these different substances are used in the present invention without requiring purification, without prior purification of the antigenic substance reacting with the heparin substance.

The double advantage of this method is, on the one hand, a reduction in the cost of carrying out the present invention because no purification step is necessary and, on the other hand, increased sensitivity and detection by fixing of biologically available heparin, which permits fixing of Ag but also of Ag already bound to their antibodies and already forming (Ag-SH-anti(Ag-SH)) complexes. For example, heparin fixed in great number to the support, thanks to SFA, will in turn be able to fix, for example, pF4 alone but also pF4 already bound to its antibody present in the plasma or the serum of the patient. Sensitivity and detection will then be increased with such a method.

Tests may, if necessary, be sensitized with a global platelet lysate coming from a platelet concentrate prepared from platelets of normal donors and obtained by traditional techniques known to those skilled in the art. This platelet lysate supplies platelet proteins in excess concentration, which permits making the antigenic target up of heparin-dependent antibodies on the substance with high affinity for the heparin substance (SFA), in the presence of an excess of heparin substance. This sensitization is due to the fact that the plasma or the serum to be tested may contain variable quantities of platelet proteins and at times in quantities insufficient for a good reaction. The platelet lysate supplies them in sufficient quantity.

The quantity of global platelet lysate used may be from several μl to 500 μl or more. As a general rule, excellent results are obtained with a platelet lysate diluted from 1:10 to 1:1000, and preferably from 1:10 to 1:100, in the reactive medium. However, the use of very small quantities (lysate diluted to 1:100000 or more) is possible for reliable diagnosis.

For making a targeted diagnosis, the serum or the plasma of the patient susceptible of having developed heparin-dependent antibodies will be added to the washed reactive mixture. If the serum or the plasma contains antibodies induced by heparin, the following reaction will take place:

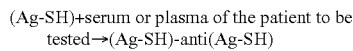

This last complex will be revealed by an appropriate known technique.

The patient's plasma (or serum) is usually tested at a dilution of between 1:1 and 1:500, but other variants are possible beyond these limits. For example, for the technology using latex particles, the serum or plasma are used pure. The reactive volume ranges from several μl to 0.5 ml. As a general rule, from less than 1 μl to 200 μl of patient serum or plasma will be used.

Advantageously, revelation of the resulting Ag-SH-anti(Ag-SH) complex may be effected by EIA tests (enzymoimmunologic assays), traditional ELISA assays or by RIA (radioimmunologic assays) but also by immunofluorescence, by immunoturbidimetry, by agglutination of latex on slides, by nephelometry, by turbidimetry or nephelometry enhanced by latex particles or by any other traditional or new technique, sensitive and known for the detection of antibodies or the formation of antigen-antibody complexes.

Figure 2:
FIG. 2 shows an immunologic reaction followed by an indicator reaction.

Immunochemistry detection methods generally use an enzymatic marker (peroxidase, glucose oxidase, alkaline phosphatase). The immunologic reaction is followed by an indicator reaction which permits photometric detection of the enzymatic activity related to the (Ag-SH)-anti(Ag-SH) complex, see FIG. 2. Usually, it is a second anti-immunoglobulin (anti-Ig) antibody that is marked by an enzyme*, and the reaction develops in the solid phase according to a non-competitive principle: (Ag-SH)-anti(Ag-SH)+anti-anti(Ag-SH)*→(Ag-SH)-anti(Ag-SH)-anti-anti(Ag-SH)*.

This enzyme* catalyzes the oxidation of a chromogenic substrate and the intensity of the coloration is proportional to the concentration of the heparin-induced antibody to be measured in the plasma or the serum of the patient. Usually, the enzyme used is peroxidase and its chromogenic substrate is OPD or ortho phenylenediamine, and more and more often TMB (tetramethylbenzidine). Depending upon the technique used, the Ag-SH-anti(Ag-SH) complex could also be revealed by fluorogenic means, a radioisotope, a colored latex particle, colloidal gold, etc.

The anti(Ag-SH) antibodies issuing from the patient's plasma, and the second anti-Ig antibodies may be polyclonal or monoclonal antibodies (IgG, IgA or IgM).

Alternatively, the antibodies may be detected directly as complexes with the antigen by means of new detection methods like refractometry, diffraction of light rays by the reactive surface, methods of modification of electrical conductivity or of the magnetic field, etc.

There is no particular constraint as to concentration for revealing the (Ag-SH)-anti(Ag-SH) complex. Concentrations of from 0.01 μg to 1 mg are used, but as a general rule, concentrations of from 0.1 to 100 μg are used.

Supports for immunologic reactions used for these tests for the detection of heparin-dependent antibodies and for the diagnosis of HIT type II according to the present invention may be of various natures and are selected from among: slides, microplates, fluorescent latexes, magnetic latexes, immunofiltration membranes or immunomigration membranes, biochips, beads, flakes, tubes, but also liposomes, lipidic vesicles, biological microparticles or microparticles obtained from polymers, or emulsions, etc.

Preferably, latex beads will be used.

The substance with high affinity for the heparin substance-heparin substance complex (or SFA-SH) is fixed to the support for immunologic reactions by adsorption or by covalent binding.

In a variant of the present invention, two substances with high affinity for heparin, such as, for example, protamine sulfate combined with polybrene or protamine sulfate combined with poly-L-lysine, will be used.

A combination of at least two substances with high affinity for heparin can be obtained by selecting these substances from among protamine sulfate, poly-L-lysine, polyarginine, polybrene or streptavidin, the heparin substance being biotinylated in this last case.

In another variant of the present invention, two heparin substances, such as, for example, non-fractionated heparin combined with pentosan polysulfate, one heparin combined with polyvinyl sulfate, will be used.

A combination of at least two heparin substances can be obtained by selecting these substances from among those mentioned in the present description.

In still another variant, two antigenic substances such as, for example, pF4 and interleukin-8 (IL-8), will be used. A combination of at least two antigenic substances may be made by selecting these substances from among those mentioned above.

These examples of combinations are of course not limitative, and other combinations of several substances with high affinity for heparin, other combinations of several heparin substances and other combinations of several antigenic substances may be used. Mixtures of these various combinations may also be used. In effect, the present invention relates to a method consisting in part of reacting at least one substance with high affinity for a heparin substance (SFA) with at least one heparin substance (SH), then with at least one antigenic substance. Each of the various combinations used gives results similar to those given in the examples below.

The present invention also relates to a kit for carrying out the method of the present invention as described above.

The said kit is a kit for the detection of heparin-dependent antibodies and the diagnosis of immune or autoimmune pathologies potentiated by a heparin substance, such as thrombocytopenias induced by a heparin substance (SH) as inducer drug, characterized in that it comprises:

at least one substance with high affinity for a heparin substance (SFA) consisting of any molecule or complex having a high affinity for a heparin substance at least one heparin substance (SH), the substance with high affinity for a heparin substance-heparin substance (SFA-SH) complex formed being designed to react with at least one antigenic substance in sufficient quantity and capable of reacting with a heparin substance thus forming the (Ag-SH) complex and a serum or a plasma potentially containing an anti(Ag-SH) antibody material, generated in the organism after administration of a heparin substance, in case of thrombocytopenia induced by heparin, and which recognizes Ag-SH, according to the reaction

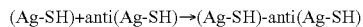

and/or at least one immune complex consisting of an Ag-SH/anti(Ag-SH) antibody complex present in the plasma or serum of the patient capable of reacting with the substance with high affinity for the heparin substance-heparin substance (SFA-SH) complex.

The characteristics of this method and of this kit for the detection of antibodies induced by heparin and the diagnosis of immune or autoimmune pathologies potentiated by a heparin substance, such as thrombocytopenia induced by heparin, will be better understood and illustrated upon reading the examples of performance which follow:

EXAMPLES OF PERFORMANCE OF THE TEST FOR THE RAPID DIAGNOSIS OF THROMBOCYTOPENIAS INDUCED BY HEPARIN(HIT)

Example 1

An ELISA plate (example MAXISORP Type 1 with NUNC or NUNC COVALINK certificate) is incubated with 200 μl (50-250 possible) in wells of a mixture of protamine sulfate (extract of salmon sperm and supplied by Sigma) at 10 μg/ml and 20 IU/ml of non-fractionated heparin (type of calciparin from Choay/Sanofi-Aventis) in 0.05 M phosphate buffer at pH 7.50 or 0.05 M carbonate buffer at pH 9.6, for 16 to 24 hours at ambient temperature or at +4° C. After washing, the plate is saturated with animal serum (goat, bovine, sheep or other) at 10-20% in 0.05 M phosphate buffer at pH 7.50. After incubation for 1 to 48 hours at ambient temperature or at +4° C., the plate is washed and used immediately, or stabilized for later use.

At the time of the test, 200 μl of the plasma or serum to be tested, diluted to 1:100 in 0.05 M phosphate buffer, 0.15 M sodium chloride and 10 to 20% animal serum (goat, bovine, sheep or other), are introduced into the wells and incubated for 1 to 2 hours at ambient temperature. After this incubation, the plates are washed and the revealer, specific antibody of human immunoglobulins IgG, or IgM or IgA coupled to peroxidase, used at 0.1 to 5 μg/ml in 0.05 M phosphate buffer, 0.15 M NaCl, 1% bovine serum albumin and at pH 7.50 (or to alkaline phosphatase) are introduced and incubated for 1 to 2 hours at ambient temperature. After a new wash, the substrate is introduced (OPD/H2O2 or TMB/H2O2 for peroxidase or PNP for alkaline phosphatase) and incubated at ambient temperature. After 2 to 30 minutes of incubation (depending upon the variant used), the reaction is halted by sulfuric acid (peroxidase), from 0.25 to 2 M or sodium hydroxide at a concentration of from 0.1 to 2 M (for alkaline phosphatase) and the OD is read at 492 nm (OPD), or at 450 nm (TMB) or at 405 nm (PNP). The presence of antibodies associated with the risk or the pathology of HIT is manifested by elevated OD readings, greater than 0.30 and usually very elevated, generally above 1.00. Normal plasmas in general have an OD of less than 0.20.

In an advantageous variant of the technique, the platelet lysate is added to the wells (50 μl of a dilution of from 1:10 to 1:1000 in 0.05 M phosphate buffer, 0.15 M NaCl at pH 7.50), or included in the diluent of the sample (patient's serum or plasma) at a dilution of from 1:10 to 1:1000. The protocol is then continued as indicated.

Example 2

An ELISA plate (example MAXISORP Type 1 with NUNC or NUNC COVALINK certificate) is incubated with 200 μl (50-250 possible) in wells of streptavidin (Roche, Mannheim, Germany) at 5 μg/ml in 0.05 M carbonate buffer at pH 9.60. After incubation for 12 to 48 hours at ambient temperature or at ° C. [sic] and washing, 200 μl in wells of biotinylated heparin (Sigma) at a concentration of from 1 to 25 IU/ml are added and incubated for 1 to 24 hours at ambient temperature or at +4° C. After being washed, the plate is saturated with animal serum (goat, bovine, sheep or other) at 10-20% in 0.05 M phosphate buffer at pH 7.50. Alternatively, commercial streptavidin plates (Roche, NUNC, Greiner, etc.) may be used for binding of the heparin. After incubation of 1 to 48 hours at ambient temperature or at +4° C., the plate is washed and used immediately, or stabilized for later use. At the time of the test, 200 μl of the plasma or serum to be tested, diluted to 1:100 in 0.05 M phosphate buffer, 0.15 M sodium chloride and 10 to 20% of animal serum (goat, bovine, sheep or other) are introduced into the wells and incubated for 1 to 2 hours at ambient temperature. After this incubation, the plates are washed and the revealer, specific antibody of human immunoglobulins IgG, or IgM or IgA coupled to peroxidase, used at a concentration of from 0.1 to 5 μg/ml in 0.05 M phosphate buffer, 0.15 M NaCl, 1% bovine serum albumin and at pH 7.50 (or to alkaline phosphatase) are introduced and incubated for 1 to 2 hours at ambient temperature. After a new wash, the substrate is introduced (OPD/H2O2 or TMB/H2O2 for peroxidase or PNP for alkaline phosphatase) and incubated at ambient temperature. After 2 to 30 minutes of incubation (depending upon the variant used), the reaction is halted by sulfuric acid (peroxidase) at from 0.25 to 2 M or sodium hydroxide at from 0.1 to 2 M (for alkaline phosphatase), and the OD is read at 492 nm (OPD), or at 450 nm (TMB) or at 405 nm (PNP). The presence of antibodies associated with the risk or with the pathology of HIT is manifested by elevated ODs, greater than 0.30 and usually very elevated, generally above 1.00. Normal plasmas in general have an OD of less than 0.20.

In an advantageous variant of the technique, the platelet lysate is added to the wells (50 μl of a dilution of from 1:10 to 1:1000 in 0.05 M phosphate buffer, 0.15 M NaCl at pH 7.50), or included in the diluent of the sample (patient's serum or plasma) at a dilution of from 1:10 to 1:1000. The protocol is then continued as indicated.

Example 3

Latex beads in polystyrene or any other polymer, ranging in size between 20 and 2000 nm, (polybutyl methacrylate) non-functionalized or derivatized (COOH, or NH2, or SH, or CHCl2, or OH, etc.) are coupled with protamine sulfate at the rate of from 0.01 to 10 mg per 100 mg of latex beads (or per ml of colloidal latex suspension of latex at 10% or per 2 ml of colloidal suspension at 5%) by simple adsorption or by covalent binding according to techniques known to those skilled in the art and available in the literature. Heparin is added at a concentration of between 1 and 1000 IU/ml. After washing, dialysis or any other appropriate treatment for removing the excess of heparin, the particles in colloidal suspension are stabilized, and brought to 0.5% in phosphate, glycine or borate buffer at 0.05 M, containing 0.15 M sodium chloride, 1% bovine serum albumin, polyethylene glycol, and if necessary a surfactant such as Tween 20 or 80 or SDS (0.01 to 0.1%).

These particles may be used for agglutination tests on slides or for photometric or nephelometric tests.

In the variant in which the platelet lysate is used for sensitizing the technique, the latter is added at a concentration of from 1:2 to 1:200 in the diluent of the sample to be tested (patient's plasma or serum) or directly to the stock solution of the colloidal latex suspension.

For tests on slides, on a glass slide 20 to 50 μl of plasma or serum to be tested, not diluted or diluted from 1:2 to 1:10, are incubated with 20 to 50 μl of latex particles sensitized by protamine sulfate and heparin and stabilized. After mixture and agitation, the appearance of agglutination is observed. It indicates the presence of antibodies.

Another use of beads consists in immunoturbidimetric or nephelometric tests. The beads are brought to 0.1% concentration in 0.05 M phosphate buffer, containing 0.15 M sodium chloride and 1% bovine serum albumin. In the test, 250 μl of beads are incubated with 250 μl of serum or plasma to be tested diluted from 1:1 to 1:100 in a 0.05 M phosphate buffer, containing 0.15 M sodium chloride, 1% bovine serum albumin and from 0.1 to 10% polyethylene glycol, at a pH of from 7.00 to 9.50. After 1 to 60 min of incubation, the variation in OD is measured at a wavelength that may range from 300 to 1000 nm. If the antibodies are present, the increase in absorbance in 60 min is greater than 0.100 and is usually between 0.200 and 2.00. This indicates the presence of heparin-dependent antibodies, which may be involved in HIT. The reaction can be sensitized by using a polymer such as polyethylene glycol (PEG) or polyvinylpyrrolidone (PVP) in the reaction buffer. In the variant in which the platelet lysate is used for sensitizing the technique, the latter is added at a concentration of from 1:2 to 1:200 to the diluent of the sample to be tested (patient's plasma or serum) or directly to the stock solution of the colloidal latex suspension.

Example 4

Beads of latex in polystyrene or any other polymer (polybutyl methacrylate), ranging in size between 20 and 2000 nm, not functionalized or derivatized (COOH, or NH2, or SH, or CHCl2, or OH, etc.) are coupled with streptavidin (Roche, Mannheim, Germany) at the rate of 0.01 to 10 mg per 100 mg of latex beads (or per ml of 10% colloidal suspension or per 2 ml of colloidal suspension at 5%) by simple adsorption or by covalent binding according to techniques known to those skilled in the art and available in the literature. Biotinylated heparin (Sigma) is then added at the rate of from 0.05 to 50 IU/ml, and incubated with the latex particles for 1 to 24 hours at ambient temperature or at +4° C.

After washing, dialysis or any other appropriate treatment for removing the excess of heparin, the particles in colloidal suspension are stabilized, and brought to 0.5% in phosphate or glycine or borate buffer at 0.05 M, containing 0.15 M sodium chloride, 1% bovine serum albumin, polyethylene glycol, and if necessary a surfactant such as TWEEN 20 or TWEEN 80 or SDS (0.01 at 0.1%).

These particles may be used for agglutination tests on slides or for photometric or nephelometric tests.

For tests on slides, on a glass slide, 20 to 50 μl of plasma or serum to be tested, not diluted or diluted from 1:2 to 1:10, are incubated with 20 to 50 μl of latex particles sensitized by streptavidin and biotinylated heparin and stabilized. After mixture and agitation, the appearance of agglutination is observed. It indicates the presence of antibodies.

In the variant in which the platelet lysate is used for sensitizing the technique, the latter is added at a concentration of from 1:2 to 1:200 to the diluent of the sample to be tested (patient's plasma or serum) or directly to the stock solution of the colloidal latex suspension.

Another use of beads consists in immunoturbidimetric or nephelometric tests. The beads are brought to 0.1% concentration in 0.05 M phosphate buffer, containing 0.15 M sodium chloride and 1% bovine serum albumin. In the test, 250 μl of beads are incubated with 250 μl of serum or plasma to be tested diluted from 1:1 to 1:100 in a 0.05 M phosphate buffer, containing 0.15 M sodium chloride, 1% bovine serum albumin and from 0.1 to 10% polyethylene glycol, at a pH of from 7.00 to 9.50.

After 1 to 60 min of incubation, the variation in OD is measured at a wavelength of from 300 to 1000 nm. If the antibodies are present, the increase in absorbance in 60 min is greater than 0.100 and usually between 0.200 and 2.00. This indicates the presence of heparin-dependent antibodies, which may be involved in HIT. The reaction may be sensitized by using a polymer such as polyethylene glycol (PEG) or polyvinylpyrrolidone (PVP) in the reaction buffer.

In the variant in which the platelet lysate is used for sensitizing the technique, the latter is added at a concentration of from 1:2 to 1:200 to the diluent of the sample to be tested (patient's plasma or serum) or directly to the stock solution of the colloidal latex suspension.

Example 5

An ELISA plate (example MAXISORP Type 1 with NUNC or NUNC COVALINK certificate) is incubated with 200 μl (50-250 possible) in wells of a mixture of protamine sulfate (extract of salmon sperm and furnished by Sigma) and poly-L-lysine of between 10 to 20 μg/ml and from 10 to 20 IU/ml of non-fractionated heparin (type of calciparin from Choay/Sanofi-Aventis) and from 50 to 100 μg of pentosan polysulfate in 0.05 M phosphate buffer at pH 7.50 or 0.05 M carbonate buffer at pH 9.6, for 16 to 24 hours at ambient temperature or at +4° C. After washing, the plate is saturated with animal serum (goat, bovine, sheep or other) at 10-20% in 0.05 M phosphate buffer at pH 7.50. After incubation of 1 to 48 hours at ambient temperature or at +4° C., the plate is washed and used immediately, or stabilized for later use.

At the time of the test, 200 µl of the plasma or the serum to be tested, diluted to 1:100 in 0.05 M phosphate buffer, 0.15 M sodium chloride and 10 to 20% animal serum (goat, bovine, sheep or other) are introduced into the wells and incubated for 1 to 2 hours at ambient temperature. After this incubation, the plates are washed and the revealer, specific antibody of human immunoglobulins IgG, or IgM or IgA coupled to peroxidase, used at 0.1 to 5 µg/ml in 0.05 M phosphate buffer, 0.15 M NaCl, 1% bovine serum albumin and at pH 7.50 (or to alkaline phosphatase) are introduced and incubated for 1 to 2 hours at ambient temperature. After a new wash, the substrate is introduced (OPD/H2O2 or TMB/H2O2 for peroxidase or PNP for alkaline phosphatase) and incubated at ambient temperature. After 2 to 30 minutes of incubation (depending upon the variant used), the reaction is halted by sulfuric acid (peroxidase) from 0.25 to 2 M or sodium hydroxide at a concentration of from 0.1 to 2 M (for alkaline phosphatase), and the OD is read at 492 nm (OPD), or at 450 nm (TMB) or at 405 nm (PNP). The presence of antibodies associated with the risk or with the pathology of HIT is manifested by elevated ODs, greater than 0.30 and usually very elevated, generally above 1.00. Normal plasmas in general have an OD below 0.20.

In an advantageous variant of the technique, the platelet lysate is added to the wells (50 µl of a dilution of from 1:10 to 1:1000 in 0.05 M phosphate buffer, 0.15 M NaCl at pH 7.50), or included in the diluent of the sample (patient's serum or plasma) at a dilution of from 1:10 to 1:1000. The protocol is then continued as indicated.

In another variant of the technique, the platelet lysate (25 µl of a dilution of from 1:10 to 1:1000 in 0.05 M phosphate buffer, 0.15 M NaCl at pH 7.50) and recombinant IL-8 (25 µl of a dilution diluted between 1 and 20 µg/ml in 0.05 M phosphate buffer, 0.15 M NaCl at pH 7.50) are added to the wells, or included in the diluent of the sample (patient's serum or plasma) at a dilution of from 1:10 to 1:1000 for the platelet lysate and from 1 to 20 µl/ml for the recombinant IL-8. The protocol is then continued as indicated.

In another variant of the technique, the platelet lysate (25 µl of a dilution of from 1:10 to 1:1000 in 0.05 M phosphate buffer, 0.15 M NaCl at pH 7.50) and the leukocyte lysate (25 µl of a dilution of from 1:10 to 1:1000 in 0.05 M phosphate buffer, 0.15 M NaCl at pH 7.50) are added to the wells, or included in the diluent of the sample (patient's serum or plasma) at a dilution of from 1:10 to 1:1000 for the platelet lysate as well as the leukocyte lysate. The protocol is then continued as indicated.

Example 6

An ELISA plate (example MAXISORP Type 1 with NUNC or NUNC COVALINK certificate) is incubated with 200 µl (50-250 possible) in wells of streptavidin (Roche, Mannheim, Germany) at 5 µg/ml in 0.05 M carbonate buffer at pH 9.60. After incubation of 12 to 48 hours at ambient temperature or at ° C. [sic] and wash, 200 µl in wells of biotinylated heparin (Sigma) at a concentration of from 1 to 25 IU/ml are added and incubated for 1 to 24 hours at ambient temperature or at +4° C. After washing, the plate is saturated with animal serum (goat, bovine, sheep or other) at 10-20% in 0.05 M phosphate buffer at pH 7.50. Alternatively, commercial streptavidin plates (Roche, NUNC, Greiner, etc.) may be used for binding the heparin. After incubation of 1 to 48 hours at ambient temperature or at +4° C., the plate is washed and used immediately or stabilized for later use. At the time of the test, 200 µl of the plasma or serum to be tested, diluted to 1:100 in 0.05 M phosphate buffer, 0.15 M sodium chloride and 10 to 20% animal serum (goat, bovine, sheep or other) are introduced into the wells and incubated for 1 to 2 hours at ambient temperature. After this incubation, the plates are washed and the revealer, specific antibody of human immunoglobulins IgG, or IgM or IgA coupled to peroxidase, used at a concentration of from 0.1 to 5 µg/ml in 0.05 M phosphate buffer, 0.15 M NaCl, 1% bovine serum albumin and at pH 7.50, (or to alkaline phosphatase) are introduced and incubated for 1 to 2 hours at ambient temperature. After a new wash, the substrate is introduced (OPD/H2O2 or TMB/H2O2 for peroxidase or PNP for alkaline phosphatase) and incubated at ambient temperature. After 2 to 30 minutes of incubation (depending upon the variant used), the reaction is halted by sulfuric acid (peroxidase) at 0.25 to 2 M or sodium hydroxide at 0.1 to 2 M (for alkaline phosphatase), and the OD is read at 492 nm (OPD), or at 450 nm (TMB) or at 405 nm (PNP). The presence of antibodies associated with the risk or the pathology of HIT is manifested by elevated ODs, greater than 0.30 and usually very elevated, generally above 1.00. Normal plasmas in general have an OD of less than 0.20.

In an advantageous variant of the technique, the platelet lysate (25 µl of a dilution of from 1:10 to 1:1000 in 0.05 M phosphate buffer, 0.15 M NaCl at pH 7.50) and recombinant IL-8 (25 µl of a solution diluted from 1 to 20 µg/ml in 0.05 M phosphate buffer, 0.15 M NaCl at pH 7.50) are added to the wells, or included in the diluent of the sample (patient's serum or plasma) at a dilution of from 1:10 to 1:1000 for the platelet lysate and between 1 and 20 µg/ml for the recombinant IL-8. The protocol is then continued as indicated.

In another variant of the technique, the platelet lysate (25 µl of a dilution of from 1:10 to 1:1000 in 0.05 M phosphate buffer, 0.15 M NaCl at pH 7.50) and the leukocyte lysate (25 µl of a dilution of from 1:10 to 1:1000 in 0.05 M phosphate buffer, 0.15 M NaCl at pH 7.50) are added to the wells, or included in the diluent of the sample (patient's serum or plasma) at a dilution of from 1:10 to 1:1000 for the platelet lysate as well as the leukocyte lysate. The protocol is then continued as indicated.

The invention claimed is:

1. A method for the detection of heparin-dependent antibodies and the diagnosis of immune or autoimmune pathologies potentiated by a heparin substance, selected from the group consisting of thrombocytopenia induced by heparin (HIT type II) as inducer drug and thrombocytopenia induced by pentosane polysulfate, said method comprises the steps of:
   (a) reacting:
      (i) at least one substance with high affinity for a heparin substance (SFA) immobilized on a solid support, consisting of any molecule or complex having a high affinity for a heparin substance;
      (ii) with at least one heparin substance (SH) so as to form a substance with high affinity for heparin-heparin substance (SFA-SH) complex, wherein the heparin substance is added in excess relative to said SFA, so as to be able to bind substances with affinity for heparin other than said SFA;
      (iii) then, after at least one washing for eliminating the at least one heparin substance not bound to said SFA;
      (iv) with a non-purified platelet lysate consisting of a non-purified concentrate of lysed platelets comprising antigenic substrates capable of reacting with the heparin substance without prior purification of said antigenic substances, and/or a non-purified leukocyte lysate comprising antigenic substances capable of reacting with the heparin substance without prior purification of said antigenic substances, or a non-purified biological medium comprising antigenic substances capable of reacting with the heparin substance without prior purification of said antigenic substances, thus forming a (Ag-SH) complex; and (v) with a non-purified plasma or a non-purified serum of a patient to be tested potentially containing a first anti(Ag-SH) antibody and generated in the tested patient's body after administration of a heparin substance and which recognizes (Ag-SH), according to the reaction:

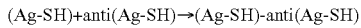

and/or at least one immune complex consisting of a second Ag-SH-anti(Ag-SH) antibody complex present in the plasma or serum of the patient capable of reacting with the substance with high affinity for the heparin substance-heparin substance (SFA-SH) complex; and (b) detecting the resulting (Ag-SH)-anti(Ag-SH) first antibody and/or second antibody complex produced after at least one washing for eliminating any substance which may interfere with a detection system corresponding to said first antibody and/or second antibody complex, thereby detecting heparin-dependent antibodies and if detected, diagnosing said immune or autoimmune pathologies potentiated by a heparin substance.

2. The method according to claim 1, wherein the at least one substance with high affinity for the heparin substance is selected from the group consisting of protamine sulfate, poly-L-lysine, and polyarginine.

3. The method according to claim 1, wherein the first antibody and/or second antibody complex are detected by EIA tests (enzymoimmunologic assays).

4. The method according to claim 1, wherein the first antibody and/or second antibody complex are detected by RIA tests (radioimmunologic assays).

5. The method according to claim 1, wherein the first antibody and/or second antibody complex are detected by immunofluorescence tests, by nephelometry, by turbidimetry, by refractometry, by diffraction of light rays by a reactive surface, by methods of modification of electrical conductivity or of a magnetic field.

6. A kit for the detection of heparin-dependent antibodies and the diagnosis of immune or autoimmune pathologies potentiated by a heparin substance, selected from the group consisting of thrombocytopenias induced by a heparin substance (SH) as inducer drug and thrombocytopenia induced by pentosane polysulfate, said kit comprises:

(a) at least one substance with high affinity for a heparin substance (SFA) immobilized on a solid support consisting of any molecule or complex having a high affinity for a heparin substance; and (b) at least one heparin substance (SH) in excess relative to the SFA, wherein the kit further comprises:

(c) an antigenic substance selected from the group consisting of a non purified platelet lysate consisting of a concentrate of non-purified lysed platelets comprising antigenic substances capable of reacting with the heparin substance without prior purification of said antigenic substances, and/or a non purified leukocyte lysate comprising antigenic substances capable of reacting with the heparin substance without prior purification of said antigenic substances, or a non purified biological medium comprising antigenic substances capable of reacting with the heparin substance, thus forming a complex (Ag-HS); the complex (SFA-SH) formed by the at least one substance with high affinity for a heparin substance (SFA) and the at least one heparin substance (SH), being designed to react with at least one antigenic substance in sufficient quantity and capable of reacting with a heparin substance thus forming the (Ag-SH) complex and a serum or a plasma of a tested patient potentially containing a first anti(Ag-SH) antibody, generated in the tested patient's body after administration of a heparin substance, in case of thrombocytopenia induced by heparin, and which recognizes Ag-SH, according to the reaction

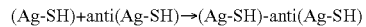

and/or at least one immune complex consisting of a second Ag-SH/anti(Ag-SH) antibody complex present in the plasma or serum of the patient capable of reacting with the substance with high affinity for the heparin substance-heparin substance (SFA-SH) complex.

7. The kit according to claim 6, wherein said at least one substance with high affinity for the heparin substance is selected from the group consisting of protamine sulfate, poly-L-lysine, polyarginine, and polybrene.

8. The kit according to claim 6, wherein the at least one heparin substance may be selected from the group consisting of non-fractionated heparin (HNF) of average molecular weight of from 6000-30000 daltons and of rotational force $[\alpha]_D^{20}$ of about +55°; heparin of low molecular weight; metallic heparinates ($Ca^{2+}$, $Li^+$, $Na^+$, $Mg^{2+}$) fragments of heparin; heparamine and its salts, chondroitins and their salts; complexes of heparin and of its derivatives or analogs; mixtures thereof; and any of the molecules above in biotinylated form.

9. The kit according to claim 6, wherein the at least one heparin substance is selected from the group consisting of pentosan polysulfate, negatively charged sulfated polysaccharide, Of polymers of sulfated polystyrene, negatively charged non-glycosaminoglycan linear polymers selected from the group consisting of polyvinyl sulfate, polyvinyl sulfonate, polyanethol sulfonate, polyvinyl phosphate and polyvinyl phosphonate, and poly-D glutamate, or their biotinylated forms.

10. The kit according to claim 6, wherein the at least one substance with high affinity for the heparin substance is fixed on a support selected from the group consisting of slides, microplates, fluorescent latexes, magnetic latexes, immunofiltration membranes or immunomigration membranes, biochips, beads, flakes, tubes, liposomes, lipidic vesicles, biological microparticles or obtained from polymers, or emulsions or any other suitable support and said fixing being effected by adsorption or by covalent bonds.

11. The kit according to claim 6, comprising a non purified platelet lysate consisting in a concentrate of lysed platelets, or a non purified leukocyte lysate.

12. The kit according to claim 6, wherein it also comprises a detection system corresponding to said antibodies for detecting the first antibody and/or second antibody complex produced.

13. The kit according to claim 12, wherein the detection system is adapted for detecting the first antibody and/or second antibody by EIA tests (enzymoimmunologic assays).

14. The kit according to claim 12, wherein the detection system is further adapted for indentifying and/or quantifying an antigen-antibody reaction or an immune complex.

15. The method according to claim 1, wherein the heparin substance (SH) comprises biotinylated heparin, and the at least one substance with high affinity for the heparin substance is streptavidin.

16. The kit according to claim 6, wherein said heparin substance (SH) comprises biotinylated heparin and said at least one substance with high affinity for the heparin substance is streptavidin.

17. A method for the detection of heparin-dependant antibodies and the diagnosis of immune or autoimmune pathologies potentiated by a heparin substance, selected from the group consisting of thrombocytopenia induced by heparin (HIT type II) as inducer drug and thrombocytopenia induced by pentosane polysulfate, said method comprises the steps of:
(a) reacting:
  (i) at least one substance with high affinity for a heparin substance (SFA) immobilized on a solid support, consisting of any molecule or complex having a high affinity for a heparin substance selected from the group consisting of protamine sulfate, poly-L-lysine, polyarginine, polybrene or streptavidin if the heparin substance is biotinylated;
  (ii) with at least one heparin substance (SH) so as to form a substance with high affinity for heparin-heparin substance (SFA-SH) complex, wherein the heparin substance is added in excess relative to said SFA, so as to be able to bind substances with affinity for heparin other than said SFA;
  (iii) then, after at least one washing for eliminating the at least one heparin substance not bound to said SFA; and
  (iv) with a non-purified plasma or a non-purified serum of a patient to be tested potentially containing antigenic substances without prior purification of said antigenic substances, and a first anti(Ag-SH) antibody and generated in the tested patient's body after administration of a heparin substance and which recognizes (Ag-SH), according to the reaction:

(Ag-SH)+anti(Ag-SH)→(Ag-SH)-anti(Ag-SH)

and/or at least one immune complex consisting of a second (Ag-SH)-anti(Ag-SH) antibody complex present in the plasma or serum of the patient capable of reacting with the substance with high affinity for the heparin substance-heparin substance (SFA-SH) complex; and
(b) detecting the resulting (Ag-SH)-anti(Ag-SH) first antibody and/or second antibody complex produced after at least one washing for eliminating any substance which may interfere with a detection system corresponding to said first antibody and/or second antibody complex, thereby detecting heparin-dependent antibodies and if detected, diagnosing said immune or autoimmune pathologies potentiated by a heparin substance.

18. The method according to claim 17, wherein the first antibody and/or second antibody complex are detected by RIA tests (radioummunologic assays).

19. The method according to claim 17, wherein the first antibody and/or second antibody complex are detected by immunofluorescence tests, by nephelometry, by turbidimetry, by refractometry, by diffraction of light rays by a reactive surface, by methods of modification of electrical conductivity or of a magnetic field.

* * * * *